US008454889B2

(12) United States Patent
Janssen et al.

(10) Patent No.: US 8,454,889 B2
(45) Date of Patent: Jun. 4, 2013

(54) GAS TREATMENT SYSTEM (75) Inventors: Robert Allen Janssen, Alpharetta, GA (US); John Gavin MacDonald, Decatur, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 721 days.

(21) Appl. No.: 11/963,237

(22) Filed: Dec. 21, 2007

(65) Prior Publication Data

US 2009/0158936 A1 Jun. 25, 2009

(51) Int. Cl.
*A61L 9/20* (2006.01)

(52) U.S. Cl.
USPC ........ 422/4; 95/149; 96/224; 96/243; 422/24; 422/121; 422/186.3

(58) Field of Classification Search
USPC ................... 96/389, 224, 243, 267, 278, 279, 96/329; 95/29, 149, 226; 422/4, 20, 24, 186.3, 422/121
See application file for complete search history.

(56) References Cited

U.S. PATENT DOCUMENTS

| | | | |
|---|---|---|---|
| 2,115,056 A | 4/1938 | Samuel | |
| 2,307,206 A | 1/1943 | Fischer | |
| 2,584,053 A | 1/1952 | Seavey et al. | |
| 2,615,692 A | 10/1952 | Muller | |
| 2,620,894 A | 12/1952 | Peterson et al. | |
| 2,661,192 A | 12/1953 | Horsley et al. | |
| 2,946,981 A | 7/1960 | O'Neill | |
| 3,066,232 A | 11/1962 | Branson | |
| 3,160,138 A | 12/1964 | Platzman | |
| 3,202,281 A | 8/1965 | Weston | |
| 3,239,998 A | 3/1966 | Carter et al. | |
| 3,246,881 A | 4/1966 | Davidson et al. | |
| 3,249,453 A | 5/1966 | Schnoring et al. | |
| 3,273,631 A | 9/1966 | Neuman | |
| 3,275,787 A | 9/1966 | Newberry | |
| 3,278,165 A | 10/1966 | Gaffney | |

(Continued)

FOREIGN PATENT DOCUMENTS

| | | |
|---|---|---|
| CA | 2175065 | 5/1995 |
| CH | 657067 | 8/1986 |

(Continued)

OTHER PUBLICATIONS

Non-final office action regarding U.S. Appl. No. 11/530,311, dated Nov. 5, 2008.

(Continued)

*Primary Examiner* — Duane Smith
(74) *Attorney, Agent, or Firm* — Armstrong Teasdale LLP (57) ABSTRACT A gas treatment system has a housing defining an interior space adapted for holding liquid therein. The housing has an inlet port and an outlet port spaced from the inlet port so that gas passing through the interior space flows through the liquid therein. A gas delivery system directs gas to be treated into the interior space of the housing at the inlet port. An ultrasonic waveguide assembly is disposed within the interior space of the housing and includes an ultrasonic horn disposed at least in part intermediate the inlet port and the outlet port of the housing. The ultrasonic horn is operable at an ultrasonic frequency to ultrasonically energize liquid within the housing. An ultraviolet light source is for emitting ultraviolet light into the interior space of the housing to treat liquid flowing from the inlet port to the outlet port.

22 Claims, 3 Drawing Sheets

U.S. PATENT DOCUMENTS

| | | | |
|---|---|---|---|
| 3,284,991 A | 11/1966 | Ploeger et al. | |
| 3,325,348 A | 6/1967 | Bennett | |
| 3,326,470 A | 6/1967 | Loudin et al. | |
| 3,338,992 A | 8/1967 | Kinney | |
| 3,341,394 A | 9/1967 | Kinney | |
| 3,425,951 A | 2/1969 | Ishiwata | |
| 3,463,321 A | 8/1969 | VanIngen | |
| 3,479,873 A | 11/1969 | Hermanns | |
| 3,490,584 A | 1/1970 | Balamuth | |
| 3,502,763 A | 3/1970 | Hartman | |
| 3,519,251 A | 7/1970 | Hammitt et al. | |
| 3,542,345 A * | 11/1970 | Kuris | 366/113 |
| 3,542,615 A | 11/1970 | Dobo et al. | |
| 3,567,185 A | 3/1971 | Ross et al. | |
| 3,591,946 A | 7/1971 | Loe | |
| 3,664,191 A | 5/1972 | Hermanns | |
| 3,692,618 A | 9/1972 | Dorschner et al. | |
| 3,782,547 A | 1/1974 | Dieter | |
| 3,802,817 A | 4/1974 | Matsuki et al. | |
| 3,865,350 A | 2/1975 | Burtis | |
| 3,873,071 A | 3/1975 | Tatebe | |
| 3,904,392 A | 9/1975 | VanIngen et al. | |
| 4,035,151 A | 7/1977 | Czerny et al. | |
| 4,062,768 A | 12/1977 | Elliot | |
| 4,070,167 A | 1/1978 | Barbee et al. | |
| 4,122,797 A | 10/1978 | Kawamura et al. | |
| 4,168,295 A | 9/1979 | Sawyer | |
| 4,218,221 A | 8/1980 | Cottell | |
| 4,249,986 A | 2/1981 | Obeda | |
| 4,259,021 A | 3/1981 | Goudy, Jr. | |
| 4,260,389 A | 4/1981 | Lister | |
| 4,266,879 A | 5/1981 | McFall | |
| 4,340,563 A | 7/1982 | Appel et al. | |
| 4,372,296 A | 2/1983 | Fahim | |
| 4,398,925 A | 8/1983 | Trinh et al. | |
| 4,425,718 A | 1/1984 | Kawaguchi | |
| 4,511,254 A | 4/1985 | North et al. | |
| 4,556,467 A | 12/1985 | Kuhn | |
| 4,612,016 A | 9/1986 | Jaeger et al. | |
| 4,612,018 A | 9/1986 | Tsuboi et al. | |
| 4,663,220 A | 5/1987 | Wisneski et al. | |
| 4,673,512 A | 6/1987 | Schram | |
| 4,693,879 A | 9/1987 | Yoshimura et al. | |
| 4,699,636 A | 10/1987 | Bofinger et al. | |
| 4,706,509 A | 11/1987 | Riebel | |
| 4,708,878 A | 11/1987 | Hagelauer et al. | |
| 4,726,522 A | 2/1988 | Kokubo et al. | |
| 4,743,361 A | 5/1988 | Schram | |
| 4,848,159 A | 7/1989 | Kennedy et al. | |
| 4,877,516 A | 10/1989 | Schram | |
| 4,879,011 A | 11/1989 | Schram | |
| 4,929,279 A | 5/1990 | Hays | |
| RE33,524 E | 1/1991 | Schram | |
| 4,983,045 A | 1/1991 | Taniguchi | |
| 5,006,266 A | 4/1991 | Schram | |
| 5,026,167 A | 6/1991 | Berliner, III | |
| 5,032,027 A | 7/1991 | Berliner, III | |
| 5,059,249 A | 10/1991 | Hays | |
| 5,096,532 A | 3/1992 | Neuwirth et al. | |
| 5,110,403 A | 5/1992 | Ehlert | |
| 5,122,165 A * | 6/1992 | Wang et al. | 95/92 |
| 5,164,094 A | 11/1992 | Stuckart | |
| 5,169,067 A | 12/1992 | Matsusaka et al. | |
| 5,242,557 A | 9/1993 | Jones et al. | |
| 5,258,413 A | 11/1993 | Isayev | |
| 5,269,297 A | 12/1993 | Weng et al. | |
| 5,326,164 A | 7/1994 | Logan | |
| 5,330,100 A | 7/1994 | Malinowski | |
| 5,335,449 A | 8/1994 | Beatty | |
| 5,372,634 A | 12/1994 | Monahan | |
| 5,373,212 A | 12/1994 | Beau | |
| 5,375,926 A | 12/1994 | Omasa | |
| 5,391,000 A | 2/1995 | Taniguchi | |
| 5,466,722 A | 11/1995 | Stoffer et al. | |
| 5,519,670 A | 5/1996 | Walter | |
| 5,536,921 A | 7/1996 | Herdrick et al. | |
| 5,583,292 A | 12/1996 | Karbach et al. | |
| 5,585,565 A | 12/1996 | Glascock et al. | |
| 5,665,383 A | 9/1997 | Grinstaff et al. | |
| 5,681,457 A | 10/1997 | Mahoney | |
| 5,711,888 A | 1/1998 | Trampler et al. | |
| 5,770,124 A | 6/1998 | Marecki et al. | |
| 5,803,270 A | 9/1998 | Brodeur | |
| 5,810,037 A | 9/1998 | Sasaki et al. | |
| 5,831,166 A | 11/1998 | Kozuka et al. | |
| 5,853,456 A | 12/1998 | Bryan et al. | |
| 5,868,153 A | 2/1999 | Cohen et al. | |
| 5,873,968 A | 2/1999 | Pike et al. | |
| 5,902,489 A | 5/1999 | Yasuda et al. | |
| 5,916,203 A | 6/1999 | Brandon et al. | |
| 5,922,355 A | 7/1999 | Parikh et al. | |
| 5,935,883 A | 8/1999 | Pike | |
| 5,937,906 A | 8/1999 | Kozyuk | |
| 5,964,926 A | 10/1999 | Cohen | |
| 5,979,664 A | 11/1999 | Brodeur | |
| 6,010,592 A | 1/2000 | Jameson et al. | |
| 6,020,277 A | 2/2000 | Jameson | |
| 6,035,897 A | 3/2000 | Kozyuk | |
| 6,053,028 A | 4/2000 | Kraus, Jr. et al. | |
| 6,053,424 A | 4/2000 | Gipson et al. | |
| 6,055,859 A | 5/2000 | Kozuka et al. | |
| 6,060,416 A | 5/2000 | Kobata | |
| 6,074,466 A | 6/2000 | Iwasa | |
| 6,090,731 A | 7/2000 | Pike et al. | |
| 6,106,590 A | 8/2000 | Ueno et al. | |
| 6,169,045 B1 | 1/2001 | Pike et al. | |
| 6,200,486 B1 * | 3/2001 | Chahine et al. | 210/748.03 |
| 6,200,488 B1 * | 3/2001 | Crowley et al. | 210/758 |
| 6,218,483 B1 | 4/2001 | Muthiah et al. | |
| 6,221,258 B1 | 4/2001 | Feke et al. | |
| 6,254,787 B1 | 7/2001 | Kimura et al. | |
| 6,266,836 B1 | 7/2001 | Gallego Juarez et al. | |
| 6,315,215 B1 | 11/2001 | Gipson et al. | |
| 6,322,240 B1 | 11/2001 | Omasa | |
| 6,332,541 B1 | 12/2001 | Coakley et al. | |
| 6,361,697 B1 | 3/2002 | Coury et al. | |
| 6,368,414 B1 | 4/2002 | Johnson | |
| 6,380,264 B1 | 4/2002 | Jameson et al. | |
| 6,383,301 B1 | 5/2002 | Bell et al. | |
| 6,450,417 B1 | 9/2002 | Gipson et al. | |
| 6,467,350 B1 | 10/2002 | Kaduchak et al. | |
| 6,482,327 B1 | 11/2002 | Mori et al. | |
| 6,506,584 B1 | 1/2003 | Chandler et al. | |
| 6,547,903 B1 | 4/2003 | McNichols et al. | |
| 6,547,935 B2 | 4/2003 | Scott | |
| 6,547,951 B1 | 4/2003 | Maekawa | |
| 6,551,607 B1 | 4/2003 | Minerath, III | |
| 6,576,042 B2 | 6/2003 | Kraus et al. | |
| 6,582,611 B1 | 6/2003 | Kerfoot | |
| 6,593,436 B2 | 7/2003 | Austin et al. | |
| 6,605,252 B2 | 8/2003 | Omasa | |
| 6,617,588 B1 * | 9/2003 | Sato | 210/748.04 |
| 6,620,226 B2 | 9/2003 | Hutton et al. | |
| 6,624,100 B1 | 9/2003 | Pike et al. | |
| 6,627,265 B2 | 9/2003 | Kutilek | |
| 6,655,826 B1 | 12/2003 | Leanos | |
| 6,659,365 B2 | 12/2003 | Gipson et al. | |
| 6,676,003 B2 | 1/2004 | Ehlert et al. | |
| 6,689,730 B2 | 2/2004 | Hortel et al. | |
| 6,739,524 B2 | 5/2004 | Taylor-McCune et al. | |
| 6,770,600 B1 | 8/2004 | Lamola | |
| 6,817,541 B2 | 11/2004 | Sands et al. | |
| 6,818,128 B2 | 11/2004 | Minter | |
| 6,837,445 B1 | 1/2005 | Tsai | |
| 6,841,921 B2 | 1/2005 | Stegelmann | |
| 6,858,181 B2 | 2/2005 | Aoyagi | |
| 6,878,288 B2 | 4/2005 | Scott | |
| 6,883,724 B2 | 4/2005 | Adiga et al. | |
| 6,890,593 B2 | 5/2005 | Tian | |
| 6,897,628 B2 | 5/2005 | Gunnerman | |
| 6,902,650 B2 | 6/2005 | Park et al. | |
| 6,911,153 B2 | 6/2005 | Minter | |
| 6,929,750 B2 | 8/2005 | Laurell et al. | |
| 6,935,770 B2 | 8/2005 | Schueler | |
| 6,936,151 B1 | 8/2005 | Lock | |
| 7,018,546 B2 * | 3/2006 | Kurihara et al. | 210/748.03 |
| 7,083,322 B2 | 8/2006 | Moore et al. | |

| Patent Number | Date | Inventor |
|---|---|---|
| 7,083,764 B2 * | 8/2006 | Scott .................... 422/186 |
| 7,090,391 B2 | 8/2006 | Taniguchi |
| 7,108,137 B2 | 9/2006 | Lal et al. |
| 7,150,779 B2 | 12/2006 | Meegan, Jr. |
| 7,156,201 B2 | 1/2007 | Peshkovskiy et al. |
| 7,293,909 B2 | 11/2007 | Taniguchi |
| 7,322,431 B2 | 1/2008 | Ratcliff |
| 7,338,551 B2 | 3/2008 | Kozyuk |
| 7,404,666 B2 | 7/2008 | Tessien |
| 7,414,009 B2 | 8/2008 | Tanaka et al. |
| 7,419,519 B2 | 9/2008 | Li et al. |
| 7,424,883 B2 | 9/2008 | McNichols et al. |
| 7,465,426 B2 | 12/2008 | Kerherve et al. |
| 7,504,075 B2 | 3/2009 | Marhasin |
| 7,516,664 B2 | 4/2009 | Meier et al. |
| 7,533,830 B1 | 5/2009 | Rose |
| 7,582,156 B2 | 9/2009 | Tanaka et al. |
| 7,673,516 B2 | 3/2010 | Janssen et al. |
| 7,703,698 B2 | 4/2010 | Janssen et al. |
| 7,712,353 B2 | 5/2010 | Janssen et al. |
| 7,735,751 B2 | 6/2010 | Ehlert et al. |
| 7,780,743 B2 | 8/2010 | Greaves et al. |
| 7,785,674 B2 | 8/2010 | Janssen et al. |
| 2001/0040935 A1 | 11/2001 | Case |
| 2002/0036173 A1 | 3/2002 | Feke et al. |
| 2002/0164274 A1 | 11/2002 | Haggett et al. |
| 2003/0042174 A1 | 3/2003 | Austin |
| 2003/0047067 A1 | 3/2003 | Kraus et al. |
| 2003/0048692 A1 | 3/2003 | Cohen et al. |
| 2003/0051989 A1 | 3/2003 | Austin |
| 2003/0061939 A1 | 4/2003 | Hutton et al. |
| 2003/0066899 A1 | 4/2003 | Gipson |
| 2003/0116014 A1 * | 6/2003 | Possanza et al. .............. 95/30 |
| 2003/0143110 A1 | 7/2003 | Kritzler |
| 2003/0194692 A1 * | 10/2003 | Purdum ..................... 435/2 |
| 2003/0234173 A1 | 12/2003 | Minter |
| 2004/0022695 A1 | 2/2004 | Simon |
| 2004/0065599 A1 | 4/2004 | Lal et al. |
| 2004/0079580 A1 | 4/2004 | Manna et al. |
| 2004/0120904 A1 | 6/2004 | Lye et al. |
| 2004/0142041 A1 | 7/2004 | MacDonald et al. |
| 2004/0187524 A1 | 9/2004 | Sen et al. |
| 2004/0202728 A1 | 10/2004 | Shanker et al. |
| 2005/0000914 A1 | 1/2005 | Dahlberg et al. |
| 2005/0008560 A1 | 1/2005 | Kataoka et al. |
| 2005/0017599 A1 | 1/2005 | Puskas |
| 2005/0025797 A1 | 2/2005 | Wang et al. |
| 2005/0042129 A1 | 2/2005 | Kazem |
| 2005/0082234 A1 | 4/2005 | Solenthaler |
| 2005/0084438 A1 | 4/2005 | Do et al. |
| 2005/0084464 A1 | 4/2005 | McGrath et al. |
| 2005/0085144 A1 | 4/2005 | MacDonald et al. |
| 2005/0092931 A1 | 5/2005 | Gadgil et al. |
| 2005/0094486 A1 | 5/2005 | Taniguchi |
| 2005/0129161 A1 | 6/2005 | Laberge |
| 2005/0207431 A1 | 9/2005 | Beca et al. |
| 2005/0220665 A1 | 10/2005 | Ding |
| 2005/0235740 A1 | 10/2005 | Desie et al. |
| 2005/0260106 A1 | 11/2005 | Marhasin |
| 2006/0000034 A1 | 1/2006 | McGrath |
| 2006/0008442 A1 | 1/2006 | MacDonald et al. |
| 2006/0120212 A1 | 6/2006 | Taniguchi et al. |
| 2007/0114306 A1 | 5/2007 | Kawakami et al. |
| 2007/0119785 A1 * | 5/2007 | Englehardt et al. ........... 210/749 |
| 2007/0131034 A1 | 6/2007 | Ehlert et al. |
| 2007/0170277 A1 | 7/2007 | Ehlert |
| 2008/0061000 A1 | 3/2008 | Janssen |
| 2008/0062811 A1 | 3/2008 | Janssen et al. |
| 2008/0063718 A1 | 3/2008 | Janssen et al. |
| 2008/0067418 A1 | 3/2008 | Ross |
| 2008/0069887 A1 | 3/2008 | Baran et al. |
| 2008/0117711 A1 | 5/2008 | Omasa |
| 2008/0155763 A1 | 7/2008 | Janssen et al. |
| 2008/0156737 A1 | 7/2008 | Janssen et al. |
| 2008/0159063 A1 | 7/2008 | Janssen et al. |
| 2008/0192568 A1 | 8/2008 | Hielscher et al. |
| 2008/0251375 A1 | 10/2008 | Hielscher et al. |
| 2009/0014377 A1 | 1/2009 | Janssen et al. |
| 2009/0147905 A1 | 6/2009 | Janssen et al. |
| 2009/0155091 A1 | 6/2009 | Ehlert et al. |
| 2009/0158936 A1 | 6/2009 | Janssen et al. |
| 2009/0162258 A1 | 6/2009 | Janssen et al. |
| 2009/0165654 A1 | 7/2009 | Koenig et al. |
| 2009/0166177 A1 | 7/2009 | Wenzel et al. |
| 2009/0168590 A1 | 7/2009 | Koenig et al. |
| 2009/0168591 A1 | 7/2009 | Wenzel et al. |
| 2009/0262597 A1 | 10/2009 | Kieffer et al. |
| 2010/0150859 A1 | 6/2010 | Do et al. |
| 2010/0206742 A1 | 8/2010 | Janssen et al. |
| 2010/0296975 A1 | 11/2010 | Peshkovsky et al. |

FOREIGN PATENT DOCUMENTS

| | | |
|---|---|---|
| CN | 1535249 A | 10/2004 |
| CN | 1247628 | 3/2006 |
| CN | 101153138 | 4/2008 |
| DE | 2131878 A1 | 2/1973 |
| DE | 262553 A3 | 12/1988 |
| DE | 9017338 | 3/1991 |
| DE | 4444525 | 6/1996 |
| DE | 19854013 | 5/2000 |
| DE | 19913397 | 9/2000 |
| DE | 19938254 | 2/2001 |
| DE | 10015144 A1 | 10/2001 |
| DE | 29825063 | 6/2004 |
| DE | 202005009923 U1 | 4/2005 |
| DE | 102004040233 | 3/2006 |
| DE | 102005025118 | 1/2007 |
| DE | 102005034629 | 1/2007 |
| EP | 0269941 A1 | 6/1988 |
| EP | 0292470 | 11/1988 |
| EP | 347891 | 12/1989 |
| EP | 0457187 A2 | 11/1991 |
| EP | 0459967 | 12/1991 |
| EP | 0625482 | 11/1994 |
| EP | 0648531 | 4/1995 |
| EP | 0894612 A2 | 2/1999 |
| EP | 1375432 A1 | 1/2004 |
| EP | 1954388 | 3/2007 |
| EP | 0983968 | 3/2008 |
| EP | 2173669 A2 | 4/2010 |
| EP | 2176173 A2 | 4/2010 |
| FR | 2793811 | 11/2000 |
| FR | 2832703 A1 | 5/2005 |
| GB | 1404575 | 9/1975 |
| JP | 56028221 | 3/1981 |
| JP | 57119853 | 7/1982 |
| JP | 58034051 | 2/1983 |
| JP | 62001413 A | 1/1987 |
| JP | 62039839 U | 3/1987 |
| JP | 63072364 | 4/1988 |
| JP | 63104664 | 5/1988 |
| JP | 1108081 | 4/1989 |
| JP | 2025602 | 1/1990 |
| JP | 02281185 A | 11/1990 |
| JP | 03053195 A | 3/1991 |
| JP | 3086258 | 4/1991 |
| JP | 03-157129 A | 5/1991 |
| JP | 6228824 | 8/1994 |
| JP | 8304388 | 11/1996 |
| JP | 9286943 | 11/1997 |
| JP | 10060331 | 3/1998 |
| JP | 11133661 | 5/1999 |
| JP | 2000158364 | 12/1999 |
| JP | 2001017970 | 1/2001 |
| JP | 2001252588 | 9/2001 |
| JP | 2003103152 A | 4/2003 |
| JP | 2004020176 | 1/2004 |
| JP | 2004256783 | 9/2004 |
| JP | 2005118688 | 5/2005 |
| KR | 20020073778 A | 9/2002 |
| KR | 1020050013858 A | 2/2005 |
| KR | 1020050113356 A | 12/2005 |
| SU | 203582 | 1/1967 |
| WO | 9400757 | 1/1994 |
| WO | 9420833 | 9/1994 |
| WO | 9429873 A | 12/1994 |
| WO | 9600318 | 1/1996 |
| WO | 9609112 A1 | 3/1996 |

| | | |
|---|---|---|
| WO | 9620017 A1 | 7/1996 |
| WO | 9743026 | 11/1997 |
| WO | 9817373 | 4/1998 |
| WO | 9844058 | 10/1998 |
| WO | 9933520 | 7/1999 |
| WO | 0004978 | 2/2000 |
| WO | 0041794 | 7/2000 |
| WO | 2001039200 A | 5/2001 |
| WO | 0222252 | 3/2002 |
| WO | 0250511 | 6/2002 |
| WO | 0280668 A2 | 10/2002 |
| WO | 03012800 | 2/2003 |
| WO | 03102737 | 12/2003 |
| WO | 2004026452 | 4/2004 |
| WO | 2004064487 | 8/2004 |
| WO | 2005014489 A1 | 2/2005 |
| WO | 2006037591 | 4/2006 |
| WO | 2006043970 A2 | 4/2006 |
| WO | 2008047259 | 4/2006 |
| WO | 2006073645 A1 | 7/2006 |
| WO | 2006074921 | 7/2006 |
| WO | 2006093804 | 9/2006 |
| WO | 2007011520 A2 | 1/2007 |
| WO | 2005011804 | 5/2007 |
| WO | 2007060245 A1 | 5/2007 |
| WO | 2007095871 | 8/2007 |
| WO | 2008029379 | 3/2008 |
| WO | 2008085806 | 7/2008 |

OTHER PUBLICATIONS

International Search Report and Written Opinion regarding PCT/IB2008/052760, dated Feb. 17, 2009.
International Search Report and Written Opinion, PCT/IB2008/055051 (Feb. 20, 2009).
International Search Report and Written Opinion from PCT/IB2008/052766, dated Mar. 31, 2009.
International Search Report and Written Opinion regarding PCT/IB2008/055394, dated Sep. 28, 2009.
Blume, T. and Neis, U. "Improved wastewater disinfection by ultrasonic pre-treatment." Ultrasonics Sonochemistry, 2004, No. 11, pp. 333-336.
International Search Report and Written Opinion for PCT/IB2008/052764 mailed Apr. 2, 2009.
International Search Report and Written Opinion regarding PCT/IB2007/054898, dated May 15, 2008.
International Search Report and Written Opinion regarding PCT/IB2008/055396, dated Jul. 29, 2009.
International Search Report and Written Opinion issued Aug. 18, 2009 for PCT/IB2008/055520.
International Search Report and Written Opinion issued Aug. 18, 2009 for PCT/IB2008/055517.
International Search Report and Written Opinion issued Aug. 18, 2009 for PCT/IB2008/055518.
European Office Action regarding European Application No. 07805228.9, dated Oct. 9, 2009.
Non-final office action regarding U.S. Appl. No. 11/617,515, dated Mar. 27, 2009.
Non-final Office action regarding U.S. Appl. No. 11/965,435, dated Mar. 11, 2010.
English translation of Nagel WO 2006/074921 A1, accessed on the EPO website.
Non-final office action regarding U.S. Appl. No. 11/950,943, dated May 1, 2009.
J.D. Lawson, "Some Criteria for a Power Producing Thermonuclear Reactor", Proc. Phys. Soc. B70, pp. 6-10 (1957).
L.A. Artsimovich, "Controlled Thermonuclear Reactions", Gordon and Breach Science Publishers, New York, first English translation, 1964.
D.R.O. Morrison, "Cold Fusion Update No. 9", Jan. 1994, from Newsgroups sci.physics.fusion, http://www.groups.google.com.
Brenner et al, Single-bubble sonoluminescence, Reviews of Modern Physics, vol. 74, Apr. 2002, pp. 425-484.
J. Lister, Plasma Physics and Controlled Fusion 48, pp. 715-716 (2006).
U.S. Department of Energy, "Report of the Review of Low Energy Nuclear Reactions", Dec. 1, 2004 (USDOE).
Final Office Action Regarding U.S. Appl. No. 11/530,311, dated Jun. 23, 2009.
International Search Report and Written Opinion regarding PCT/IB2007/054892 dated May 15, 2008.
Non-final office action regarding U.S. Appl. No. 11/617.497, dated Jun. 26, 2009.
International Search Report and Written Opinion regarding PCT/IB2008/055395, dated Sep. 14, 2009.
International Search Report and Written Opinion regarding PCT/IB2008/055514, dated Aug. 25, 2009.
Non-final Office Action regarding U.S. Appl. No. 12/335,231, dated Oct. 15, 2009.
Kloeppel, James E. "Temperature inside collapsing bubble four times that of the sun," News Bureau, University of Illinois at Urbana-Champaign.
Oct. 27, 2010 Letter regarding the Office action issued for Mexican Patent Application Serial No. MX/a/2009/002519 mailed Oct. 12, 2010.
Non-final Office action regarding U.S. Appl. No. 11/530,183, dated Apr. 19, 2010.
Takehi Moriguchi, et al. "Metal-modified silica adsorbents for removal of humic substances in water." Journal of Colloid and Interface Science 283, 2005 300-310, See Abstract, pp. 301 and 304.
International Search Report and Written Opinion regarding PCT/IB2009/055090, dated Jul. 16, 2010.
International Search Report and Written Opinion regarding PCT/IB2009/055092, dated Jul. 16, 2010.
First Office Action for China Patent Application No. 200780033331.3, dated Nov. 14, 2011.
First Office Action for China Patent Application No. 200880121407.2, dated Aug. 24, 2011.
Non-final Office action issued in U.S. Appl. No. 11/963,139, dated Feb. 18, 2011.
Non-final Office action issued in U.S. Appl. No. 11/777,140, dated Feb. 23, 2011.
Non-final Office Action issued in U.S. Appl. No. 11/777,151 mailed Dec. 8, 2010.
Final Office Action issued in U.S. Appl. No. 11/966,418 mailed Jan. 12, 2011.
Non-final Office Action received in U.S. Appl. No. 11/966,458 mailed Sep. 28, 2010.
Non-final Office Action submitted in U.S. Appl. No. 11/530,183 dated Oct. 13, 2010.
Final Office action issued in U.S. Appl. No. 11/966,447 mailed Jan. 5, 2011.
Supplementary European Search Report issued in EP Application No. 08789242 mailed Dec. 17, 2010.
Compton R G et al., "Electrode Processes at the Surfaces of Sonotrodes," Electrochimica ACTA, vol. 41, No. 2, pp. 315-320 (Feb. 1, 1996).
Extended European Search Report received in EP Patent Application No. 08789246.9 mailed Nov. 30, 2011.
Extended European Search Report received in EP Patent Application No. 08789248.5 dated Nov. 30, 2011.
Chinese First Office Action for Patent Application No. 200880123174.X dated Sep. 20, 2012; 8 pages.
Chinese First Office Action for Patent Application No. 200880123172.0 dated Oct. 10, 2012; 9 pages.
Extended European Search Report received in EP Patent Application No. 08868425 dated Feb. 14, 2012.
EP Office Action for Patent Application No. 08 789 246.9-2104 dated Sep. 4, 2012; 4 pages.
EP Office Action for Patent Application No. 08 789 248.5-2104 dated Sep. 4, 2012; 4 pages.
Final Office Action issued in U.S. Appl. No. 11/966,458, dated Mar. 17, 2011.
Final Office Action issued in U.S. Appl. No. 11/530,183, dated Mar. 22, 2011.
Non-Final Office Action issued in U.S. Appl. No. 11/966,472, dated Mar. 31, 2011.

Final Office Action issued in U.S. Appl. No. 12/335,231, dated Mar. 31, 2011.
Barbaglia et al., "Search of Fusion Reactions During the Cavitation of a Single Bubble in Deuterated Liquids," Physica Scripta 72, pp. 75-78 (2005).
Final Office Action issued in U.S. Appl. No. 11/777,140, dated Dec. 1, 2010.
Non-Final Office Action issued in U.S. Appl. No. 11/530,210, dated Dec. 1, 2010.
Non-Final Office Action issued in U.S. Appl. No. 11/530,210, dated Jun. 28, 2010.
Sivakumar et al., "Preparation of nanosized TiO2 Supported on Activated Alumina by a Sonochemical Method: Observation of an Increased Photocatalytic Decolourisation Efficiency," Research on Chemical Intermediated, 30 (7-8):785-792, 2004.
Kuo et al., "Nano-particles Dispersion Effect on Ni/Al2O3 Composite Coatings," Materials Chemistry and Physics, 86:5-10 (2004).
Non-Final Office Action issued in U.S. Appl. No. 12/704,058, dated Dec. 9, 2010.
International Search Report and Written Opinion regarding PCT/IB2007/052947, dated Mar. 12, 2008.
International Search Report and Written Opinion regarding PCT/IB2007/052945, dated Feb. 1, 2008.
International Search Report and Written Opinion regarding PCT/IB2007/052988, dated Feb. 14, 2008.
Taleyarkhan, et al., "Evidence for Nuclear Emissions During Acoustic Cavitation," Science, (Mar. 8, 2002), vol. 295, pp. 1868-1873.
Kloeppel, James E. "Temperature inside collapsing bubble four times that of the sun," News Bureau, University of Illinois at Urbana-Champaign, Mar. 2, 2005.
Tal-Figiel B., The Formation of Stable W/O, O/W, W/O/W Cosmetic Emulsions in an Ultrasonic Field, viewed at http://www.atypon-link.com/ICHEME/doi/abs/10.1205/cherd06199 on Oct. 19, 2007.
"Controlled Thermonuclear Fusion" viewed at http://library.thinkquest.org/17940/texts/fusion_controlled/fusion_controlled.html on Oct. 23, 2007.
Flannigan, "Measurement of Pressure and Density Inside a Single Sonoluminescing Bubble," Physical Review Letters (May 26, 2006), PRL 96.
Taleyarkhan, et al. "Additional Evidence of Nuclear Emissions During Acoustic Cavitation," Physical Review E, (Mar. 2004). vol. 69.
"Thermonuclear Fusion Energy Source for Future Generations," viewed at http://nature.com/news/2006/060109/full/060109-5.html on May 4, 2007.
Lahey, Taleyarkhan, and Nigmatulin, "Bubble Power, "IEEE spectrum, May 2005, pp. 39-43.
International Search Report and Written Opinion regarding PCT/IB2007/053621, dated Feb. 14, 2008.
International Search Report and Written Opinion regarding PCT/IB2007/053623, dated Feb. 14, 2008.
International Search Report and Written Opinion regarding PCT/IB2007/053622, dated Feb. 14, 2008.
U.S. Appl. No. 11/777,140, filed Jul. 12, 2007.
U.S. Appl. No. 11/617,497, filed Dec. 28, 2006.
U.S. Appl. No. 11/617,515, filed Dec. 28, 2006.
U.S. Appl. No. 11/777,151, filed Jul. 12, 2007.
U.S. Appl. No. 11/950,943, filed Dec. 5, 2007.
U.S. Appl. No. 11/963,139, filed Dec. 21, 2007.
U.S. Appl. No. 11/966,458, filed Dec. 28, 2007.
U.S. Appl. No. 11/966,472, filed Dec. 28, 2007.
U.S. Appl. No. 11/966,418, filed Dec. 28, 2007.
U.S. Appl. No. 11/966,447, filed Dec. 28, 2007.
U.S. Appl. No. 11/777,145, filed Dec. 12, 2007.
U.S. Appl. No. 11/965,435, filed Dec. 27, 2007.
Peplow, Mark, "Desktop fusion is back on the table," viewed at http//nature.com/news/2006/060109/full/060109-5.html on May 4, 2007.
Chinese First Office Action for 200880123165.0 dated Oct. 10, 2012; 9 pages.
Non-final Office action issued in related U.S. Appl. No. 11/777,140 on Aug. 9, 2010.
Non-Final Office action issued in related U.S. Appl. No. 11/966,418 on Aug. 2, 2010.
Non-Final Office action issued in related U.S. Appl. No. 11/966,447 on Aug. 2, 2010.
Sivakumar et al., "Preparation of nanosized TiO2 Supported on Activated Alumina by a Sonochemical Method: Observation of an Increased Photocatalytic Decolourisation Efficiency," Research on Chemical Intermediated, 30 (7-8):785-792.
Final Office Action issued for U.S. Appl. No. 11/530,210, mailed Apr. 19, 2011.
First Office Action for China Patent Application No. 20088016947.3, dated Jun. 24, 2011.
First Office Action for Russian Patent Application No. 2009112526, dated Apr. 28, 2011.
Final Office Action issued for U.S. Appl. No. 11/530,210, mailed Jul. 1, 2011.
Non-Final Office Action issued for U.S. Appl. No. 12/335,231, mailed Jul. 13, 2011.
Non-Final Office Action issued for U.S. Appl. No. 12/335,176, mailed Jul. 13, 2011.
Non-Final Office Action issued for U.S. Appl. No. 11/963,139, mailed Jun. 15, 2011.
Non-final Office Action received in U.S. Appl. No. 12/438,317, mailed Sep. 24, 2012.
Extended European Search Report for EP Patent Application No. 08867871.9, mailed Sep. 27, 2012.

* cited by examiner

GAS TREATMENT SYSTEM

FIELD

The present disclosure relates generally to systems for treating gas, and more particularly to systems for treating gas using ultrasonic energy.

BACKGROUND

It is common for various gases to be treated to remove impurities therefrom. For example, ambient air may contain impurities in the form of organics and/or microorganisms in the form of airborne or other gas entrained contaminations or pollutants or other impurities. In some instances, it is desirable to remove or eliminate these impurities before subsequent use of the gas or releasing the gas into the environment.

There are a number of known treatment technologies for treating gases to remove or eliminate impurities. Many of these technologies, however, are costly to purchase, operate, and maintain. In addition, they are often time consuming and relatively inefficient, and/or ineffective in their treatment of the impurities within the gas. For example, one known treatment method is to pass the gas to be treated through a filter. However, filtration of the impurities from the gas is limited by the pore size in the filter media and the ability of the filter to entrap impurities. That is, if the impurities (e.g., organics or microorganisms) are smaller than the pore size of the filter media the impurities will pass through the filter media.

SUMMARY

In one aspect, a gas treatment system comprises a housing defining an interior space. The interior space is adapted for holding liquid therein. The housing has at least one gas inlet port for receiving gas into the interior space of the housing and at least one gas outlet port for allowing gas to exit the interior space of the housing. The gas outlet port is spaced from the gas inlet port so that gas passing through the interior space of the housing from the gas inlet port to the gas outlet port flows through the liquid therein. A gas delivery system directs gas to be treated into the interior space of the housing at the gas inlet port. An ultrasonic waveguide assembly is disposed within the interior space of the housing and comprises an ultrasonic horn disposed at least in part intermediate the gas inlet port and the gas outlet port of the housing. The ultrasonic horn is operable at an ultrasonic frequency to ultrasonically energize liquid within the housing. An ultraviolet light source is for emitting ultraviolet light into the interior space of the housing to treat liquid flowing from the inlet port to the outlet port.

In another aspect, a gas treatment system generally comprises a housing defining an interior space. The housing comprises at least one gas inlet port for receiving gas to be treated into the interior space of the housing and at least one gas outlet port for allowing gas to exit the interior space of the housing. The gas outlet port is spaced from the gas inlet port so that gas passes through the interior space of the housing from the gas inlet port to the gas outlet port. At least one liquid inlet port is for receiving liquid into the interior space of the housing and at least one liquid outlet port is for allowing liquid to exit the interior space of the housing. The liquid outlet port is spaced from the liquid inlet port so that liquid flows through the interior space of the housing from the liquid inlet port to the liquid outlet port. A mixing zone within the housing is for mixing the gas and liquid within the interior space of the housing to form a gas-liquid solution. An ultrasonic horn is disposed within the interior space of the housing. The ultrasonic horn is operable at an ultrasonic frequency to ultrasonically energize the gas-liquid solution within the housing. An ultraviolet light source is for emitting ultraviolet light onto the liquid while the liquid is ultrasonically energized by the ultrasonic horn.

In yet another aspect, a process of treating a gas generally comprises delivering a gas to be treated to an interior space of a housing. The housing has at least one gas inlet port for receiving the gas into the interior space of the housing and at least one gas outlet port for allowing the gas to exit the interior space of the housing. The gas outlet port is spaced from the gas inlet port. The gas is mixed with a liquid within the interior space of the housing to form a gas-liquid solution. An ultrasonic horn disposed within the interior space of the housing is operated at an ultrasonic frequency to ultrasonically energize the gas-liquid solution within the housing. The energized gas-liquid solution is irradiated using an ultraviolet light source.

BRIEF DESCRIPTION OF THE DRAWINGS

Corresponding reference characters indicate corresponding parts throughout the drawings.

DETAILED DESCRIPTION OF THE INVENTION

Figure 1:
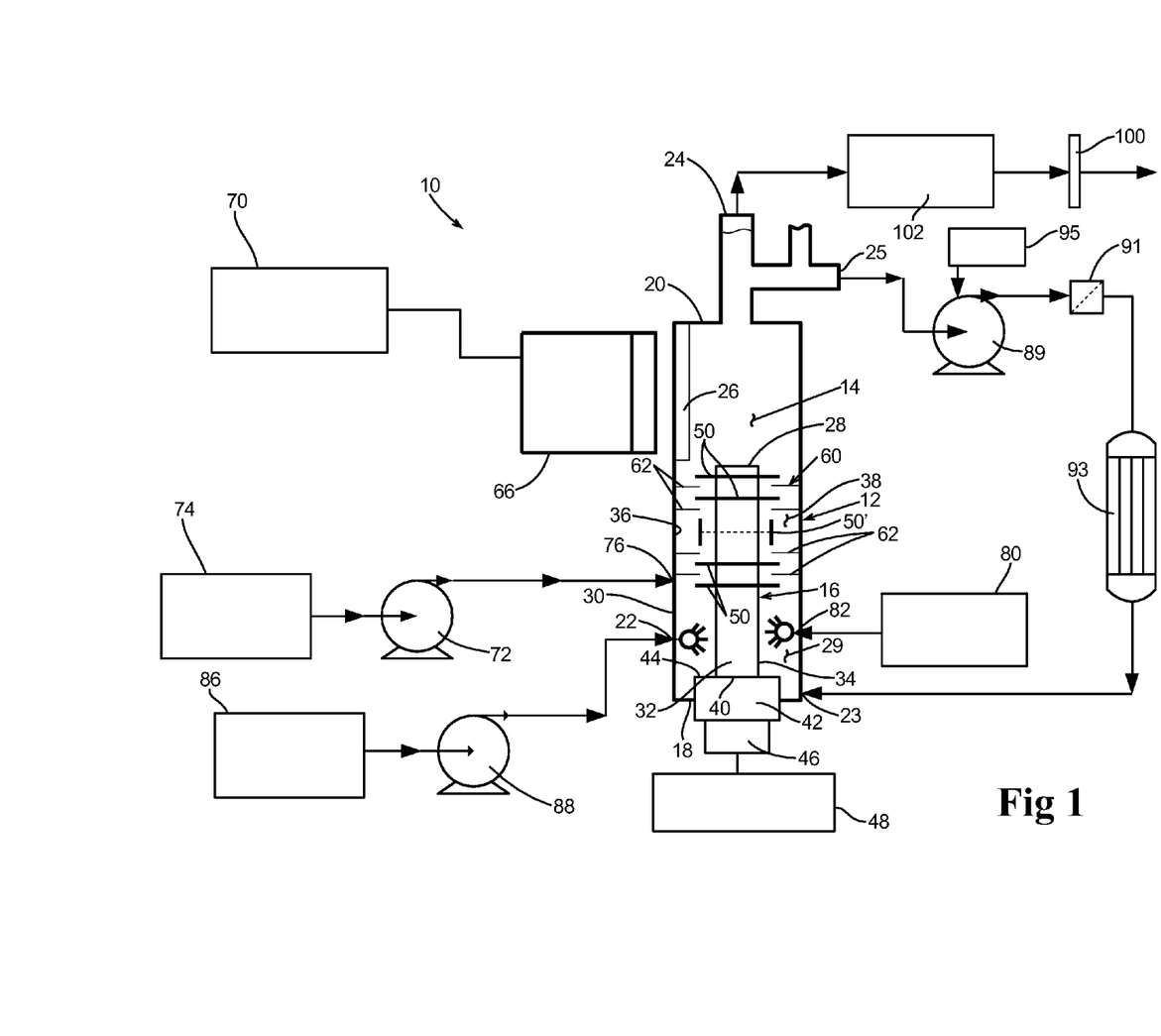
FIG. 1 is a schematic of one embodiment of a gas treatment system for treating a gas.

With particular reference now to FIG. 1, one embodiment of a gas treatment system for treating a gas, such as ambient air, passing through the system is indicated generally at 10. The term "gas", as used herein, is intended to refer to a single component gas or a gas mixture comprised of two or more gaseous components. In one suitable embodiment, the gas treated by the gas treatment system 10 may be ambient air having one or more impurities. It is understood, however, that the gas treatment system 10 can be used to treat other types of gases having impurities therein including, but not limited to, medical air, aircraft/spacecraft air, industrial emissions. The gas treatment system 10 disclosed herein may be used by itself or may be a component of a larger gas treatment process.

In one suitable embodiment, as illustrated in FIG. 1, the gas treatment system 10 comprises an ultrasonic treatment housing (or chamber), indicated generally at 12, defining an interior space 14 for receiving at least a portion of a waveguide assembly, indicated generally at 16. The housing 12 is generally elongate and has an inlet end 18 (a lower end in the orientation of the illustrated embodiment) and an outlet end 20 (an upper end in the orientation of the illustrated embodiment).

The housing 12 has one or more gas inlet ports 22 (one such gas inlet port being illustrated in FIG. 1) formed therein through which gas to be treated within the housing is delivered to the interior space 14 thereof. It will be understood by one skilled in the art that the inlet end 18 of the housing 12 may include more than one gas inlet port 22 and remain within the scope of this invention. For example, although not shown, the housing 12 may comprise two gas inlet ports, wherein the first gas inlet port and the second gas inlet port are suitably in parallel, spaced relationship with each other. In one suitable embodiment, each gas inlet port may comprise one or more air spargers, which divides the gas into numerous small bubbles as it is being introduced into the interior space 14 of the housing 12. The housing 12 also has at least one gas outlet port 24 at the outlet end 20 thereof for allowing gas to exit the interior space 14 of the housing. Thus, gas flows into the interior space 14 of the housing 12 through the gas inlet port 22, passes through the interior space, and exists through the gas outlet port 24.

The housing 12 also has one or more liquid inlet ports 23 (one such liquid inlet port being illustrated in FIG. 1) formed therein through which liquid is delivered to the interior space 14 thereof. It will be understood by one skilled in the art that the inlet end 18 of the housing 12 may include more than one liquid inlet port 23 and remain within the scope of this invention. For example, although not shown, the housing 12 may comprise two liquid inlet ports, wherein the first liquid inlet port and the second liquid inlet port are suitably in parallel, spaced relationship with each other. The housing 12 also has at least one liquid outlet port 25 at the outlet end 20 thereof for allowing liquid to exit the interior space 14 of the housing. The liquid outlet port 25 is positioned vertically below the gas outlet port 23. The relative positioning of the outlet ports 24, 25 allows the gas and liquid to separate by gravity upon exiting the housing 12. Thus, liquid flows into the interior space 14 of the housing 12 through the liquid inlet port 23, flows through the interior space, and exists through the liquid outlet port 25. It is understood that the gas treatment system 10 may instead have other suitable gas/liquid separation arrangements.

The term "liquid", as used herein, is intended to refer to a single component liquid, a solution comprised of two or more components in which at least one of the components is a liquid such as a liquid-liquid mixture, a liquid-gas mixture or a liquid in which particulate matter is entrained, or other viscous fluids. In one suitable embodiment, the liquid is water but it is understood that other types of liquids can be used without departing from the scope of this invention.

The housing 12 is configured such that gas and liquid enter the interior space 14 of the housing adjacent the inlet end 18 thereof, and mixes together to form a gas-liquid solution that flows generally longitudinally within the housing (e.g., upward in the orientation of illustrated embodiment) and exits the housing generally at the outlet end 20 of the housing. More particularly, the interior space 14 of the housing has a liquid intake zone 29 in which initial swirling of gas and liquid within the interior space 14 of the housing 12 occurs. The mixing of the gas and liquid is facilitated by the swirling action caused by the gas and liquid being mixed entering the housing 12. Moreover, the air is delivered into the interior space 14 of the housing 12 through the gas inlet port 22 by an air sparger (not shown), which also facilitates the mixing of the air and the liquid. It is understood that other types of mechanical mixing apparatus can be used to mix the gas and liquid together to form a gas-liquid solution. It is also understood that the gas and liquid may be mixed to form a gas-liquid solution before entering the interior space 14 of the housing 12, for example, with an inline mixing system.

In the illustrated embodiment, the housing 12 is generally cylindrical, thereby having a generally annular cross-section. However, it is contemplated that the cross-section of the housing 12 may be other than annular, such as polygonal or another suitable shape, and remain within the scope of this disclosure. As described below, at least a portion 26 of the illustrated housing 12 is suitably constructed of a transparent material. In the illustrated embodiment, the portion 26 of the housing 12 is constructed of quartz glass while the remainder of the housing is constructed of stainless steel. It is understood, however, that the housing 12 may be constructed from any suitable material as long as the material is compatible with the gas-liquid solution in the housing, the pressure at which the housing is intended to be subjected to during operation, and other system conditions such as temperature.

With reference still to FIG. 1, the waveguide assembly 16 extends longitudinally at least in part within the interior space 14 of the housing 12 to ultrasonically energize the gas-liquid solution flowing through the interior space of the housing. In particular, the waveguide assembly 16 of the illustrated embodiment extends longitudinally from the inlet end 18 of the housing 12 up into the interior space 14 thereof to a terminal end 28 of the waveguide assembly, which is disposed intermediate the inlets port 22, 23 and the outlet ports 24, 25. Although illustrated in FIG. 1 as extending longitudinally into the interior space 14 of the housing 12, it is understood that the waveguide assembly 16 may extend laterally from a sidewall 30 of the housing, running horizontally through the interior space thereof. Typically, the waveguide assembly 16 is mounted, either directly or indirectly, to the housing 12 as will be described later herein.

Figure 2:
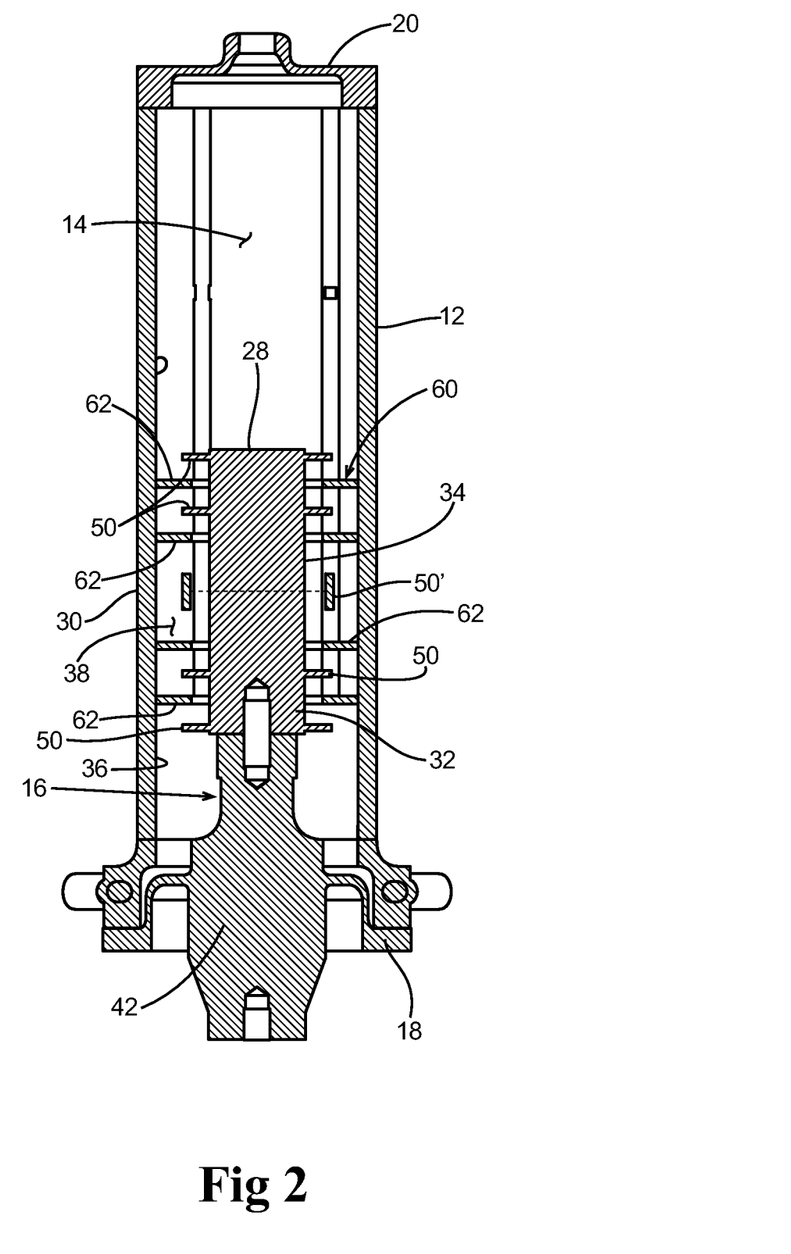
FIG. 2 is a longitudinal (e.g., vertical) cross-section of a housing of the system of FIG. 1 and illustrating an ultrasonic horn and a baffle assembly therein.

With reference now to FIGS. 1 and 2, the waveguide assembly 16 suitably comprises an elongate ultrasonic horn 32 disposed within the interior space 14 of the housing 12 intermediate the inlet ports 22, 23 and the outlet ports 24, 25 for complete submersion within the gas-liquid solution, and more suitably, in the illustrated embodiment, it is aligned coaxially with the housing. The ultrasonic horn 32 has an outer surface 34 that together with an inner surface 36 of the sidewall 30 of the housing 12 defines a flow path 38 within the interior space 14 of the housing along which the gas-liquid solution flow past the ultrasonic horn within the housing (this portion of the flow path being broadly referred to herein as the ultrasonic treatment zone).

The ultrasonic horn 32 has an upper end defining the terminal end 28 of the waveguide assembly 16 and a longitudinally opposite lower end 40. It is particularly suitable that the waveguide assembly 16 also comprises a booster 42 coaxially aligned with and connected at an upper end 44 thereof to the lower end 40 of the ultrasonic horn 32. It is understood, however, that the waveguide assembly 16 may comprise only the ultrasonic horn 32 and remain within the scope of this disclosure. It is also contemplated that the booster 42 may be disposed entirely exterior of the housing 12, with the ultrasonic horn 32 mounted on the housing without departing from the scope of this disclosure.

The waveguide assembly 16, and more particularly the booster 42, is suitably mounted on the housing 12 at the inlet end 18 thereof by a mounting member (not shown) that is configured to vibrationally isolate the waveguide assembly (which vibrates ultrasonically during operation thereof) from the housing. That is, the mounting member inhibits the transfer of longitudinal and transverse mechanical vibration of the waveguide assembly 16 to the housing 12 while maintaining the desired transverse position of the waveguide assembly (and in particular the ultrasonic horn 32) within the interior space 14 of the housing and allowing both longitudinal and transverse displacement of the ultrasonic horn 32 within the housing. The mounting member also at least in part (e.g., along with the booster 42 and/or lower end 40 of the ultrasonic horn 32) closes the inlet end 18 of the housing 12. Examples of suitable mounting member configurations are illustrated and described in U.S. Pat. No. 6,676,003, the entire disclosure of which is incorporated herein by reference to the extent it is consistent herewith.

In one suitable embodiment, the mounting member is of single-piece construction. Even more suitably, the mounting member may be formed integrally with the booster 42 (and more broadly with the waveguide assembly 16). However, it is understood that the mounting member may be constructed separately from the waveguide assembly 16 and remain within the scope of this disclosure. It is also understood that one or more components of the mounting member may be separately constructed and suitably connected or otherwise assembled together.

The mounting member may be further constructed to be generally rigid (e.g., resistant to static displacement under load) so as to hold the waveguide assembly 16 in proper alignment within the interior space 14 of the housing 12. For example, the rigid mounting member in one embodiment may be constructed of a non-elastomeric material, more suitably metal, and even more suitably the same metal from which the booster (and more broadly the waveguide assembly 16) is constructed. The term "rigid" is not, however, intended to mean that the mounting member is incapable of dynamic flexing and/or bending in response to ultrasonic vibration of the waveguide assembly 16. In other embodiments, the rigid mounting member may be constructed of an elastomeric material that is sufficiently resistant to static displacement under load but is otherwise capable of dynamic flexing and/or bending in response to ultrasonic vibration of the waveguide assembly 16.

A suitable ultrasonic drive system includes at least an exciter 46 and a power source 48 disposed exterior of the housing 12 and operatively connected to the booster 42 to energize the waveguide assembly 16 to mechanically vibrate ultrasonically. In one embodiment, the drive system is capable of operating the waveguide assembly 16 at a frequency in the range of about 15 kHz to about 100 kHz, more suitably in the range of about 15 kHz to about 60 kHz, and even more suitably in the range of about 20 kHz to about 40 kHz. Such ultrasonic drive systems are well known to those skilled in the art and need not be further described herein. Examples of suitable ultrasonic drive systems include a Model 20A3000 system available from Dukane Ultrasonics of St. Charles, Ill., and a Model 2000CS system available from Herrmann Ultrasonics of Schaumburg, Ill.

Figure 3:
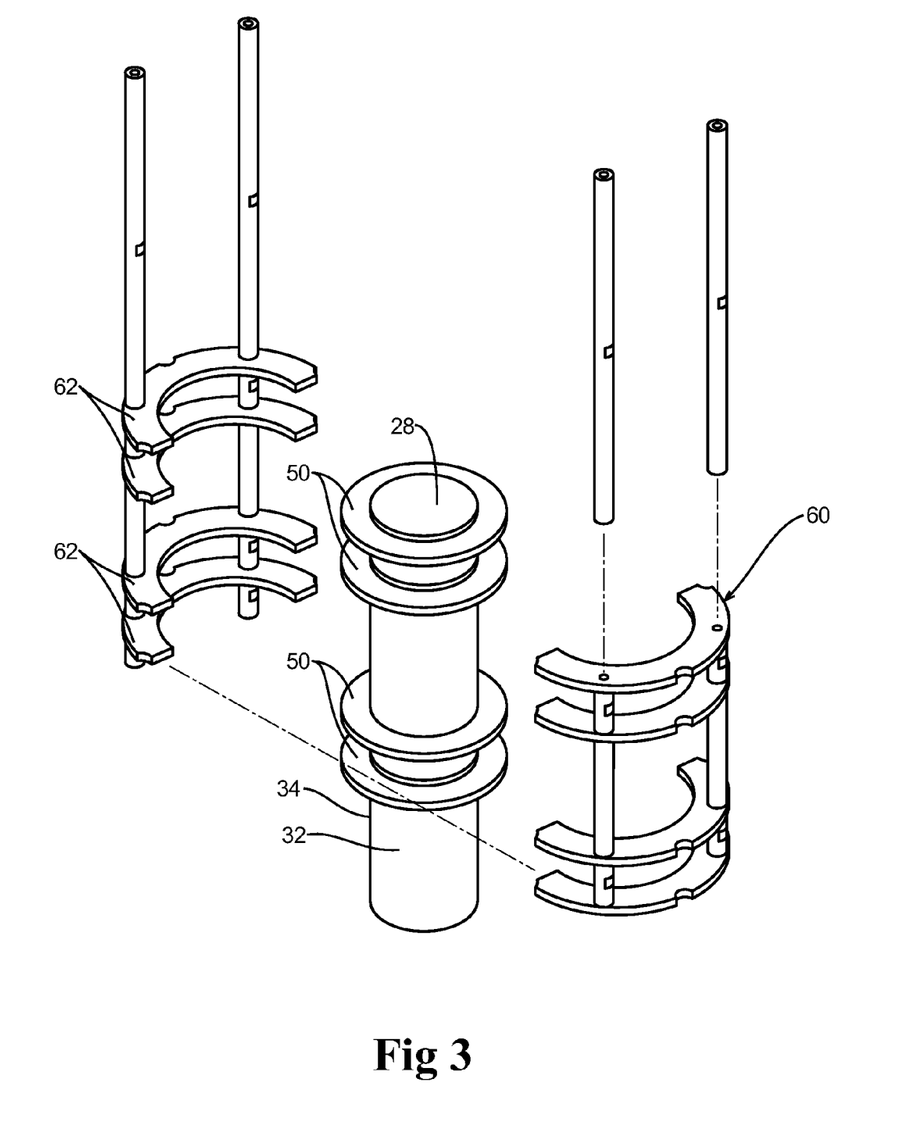
FIG. 3 is an exploded perspective of the ultrasonic horn and the baffle assembly of FIG. 2.

With particular reference to FIGS. 2 and 3, the ultrasonic horn 32 has two or more (i.e., a plurality of) agitating members 50, 50' connected to the ultrasonic horn 32 and extending at least in part transversely outward from the outer surface 34 of the ultrasonic horn in longitudinally spaced relationship with each other. Five such agitating members 50, 50' can be seen in FIG. 1. The ultrasonic horn 32 is suitably sized to have a length equal to about one-half of the resonating wavelength (otherwise commonly referred to as one-half wavelength) of the ultrasonic horn. It is understood, however, that the ultrasonic horn 32 may be sized to have any increment of one-half wavelength without departing from the scope of this disclosure.

In the illustrated embodiment, four of the five agitating members 50 comprise a series of four washer-shaped rings that extend continuously about the circumference of the ultrasonic horn 32 in longitudinally spaced relationship with each other and transversely (e.g., radially in the illustrated embodiment) outward from the outer surface 34 of the ultrasonic horn. In this manner, the vibrational displacement of each of the agitating members 50 relative to the ultrasonic horn 32 is relatively uniform about the circumference of the ultrasonic horn. It is understood, however, that the agitating members 50 need not be continuous about the circumference of the ultrasonic horn 32. For example, the agitating members 50 may instead be in the form of spokes, blades, fins or other discrete structural members that extend transversely outward from the outer surface 34 of the ultrasonic horn 32.

As illustrated in FIG. 1, the other one of the agitating members 50' (i.e., the central agitating member) has a T-shape. Specifically, the agitating member 50' disposed at a nodal region of the ultrasonic horn 32, as described more fully below, has a T-shape. It has been found that agitating members 50' having a T-shape, generate a strong radial (e.g., horizontal) acoustic wave that further increases the cavitation effect as described more fully herein.

It is understood that the number of agitating members 50, 50' (e.g., the four rings and one T-shaped member in the illustrated embodiment) may be less than or more than five without departing from the scope of this disclosure. It is also understood that the longitudinal spacing between the agitating members 50, 50' may be other than as illustrated in FIG. 1 and described above (e.g., either closer or spaced further apart). Furthermore, while the agitating members 50, 50' illustrated in FIG. 1 are equally longitudinally spaced from each other, it is alternatively contemplated that where more than two agitating members are present the spacing between longitudinally consecutive agitating members need not be uniform to remain within the scope of this disclosure.

The locations of the agitating members 50, 50' along the length of the ultrasonic horn 32 are at least in part a function of the intended vibratory displacement of the agitating members upon vibration of the ultrasonic horn. For example, in the illustrated embodiment of FIG. 1, the ultrasonic horn 32 has a nodal region located generally longitudinally centrally of the ultrasonic horn. As used herein, the "nodal region" of the ultrasonic horn 32 refers to a longitudinal region or segment of the ultrasonic horn along which little (or no) longitudinal displacement occurs during ultrasonic vibration of the ultrasonic horn and transverse (e.g., radial in the illustrated embodiment) displacement of the ultrasonic horn is generally maximized. Transverse displacement of the ultrasonic horn 32 suitably comprises transverse expansion of the ultrasonic horn but may also include transverse movement (e.g., bending) of the ultrasonic horn.

In the illustrated embodiment of FIG. 1, the configuration of the one-half wavelength ultrasonic horn 32 is such that the nodal region is particularly defined by a nodal plane (i.e., a plane transverse to the ultrasonic horn at which no longitudinal displacement occurs while transverse displacement is generally maximized) is present. This plane is also sometimes referred to as a "nodal point". Accordingly, agitating members 50 (e.g., in the illustrated embodiment, the rings) that are disposed longitudinally further from the nodal region of the ultrasonic horn 32 will experience primarily longitudinal displacement while the agitating member 50' that are longitudinally nearer to or at the nodal region (e.g., the T-shaped agitating member) will experience an increased amount of transverse displacement and a decreased amount of longitudinal displacement relative to the longitudinally distal agitating members. It is understood that the ultrasonic horn 32 may be configured so that the nodal region is other than centrally located longitudinally on the ultrasonic horn member without departing from the scope of this disclosure. It is also understood that one or more of the agitating members 50, 50' may be longitudinally located on the ultrasonic horn so as to experience both longitudinal and transverse displacement relative to the ultrasonic horn 32 upon ultrasonic vibration of the ultrasonic horn.

The agitating members 50, 50' are sufficiently constructed (e.g., in material and/or dimension such as thickness and transverse length, which is the distance that the agitating member extends transversely outward from the outer surface 34 of the ultrasonic horn 32) to facilitate dynamic motion, and in particular dynamic flexing/bending of the agitating members in response to the ultrasonic vibration of the ultrasonic horn. In one particularly suitable embodiment, for a given ultrasonic frequency at which the waveguide assembly 16 is to be operated in the housing (otherwise referred to herein as the predetermined frequency of the waveguide assembly) and a particular gas-liquid solution to be treated within the housing 12, the agitating members 50, 50' and ultrasonic horn 32 are suitably constructed and arranged to operate the agitating members in what is referred to herein as an ultrasonic cavitation mode at the predetermined frequency.

As used herein, the ultrasonic cavitation mode of the agitating members 50, 50' refers to the vibrational displacement of the agitating members sufficient to result in cavitation of the liquid flowing through the housing 12 at the predetermined ultrasonic frequency. For example, where the liquid flowing within the housing 12 comprises an air-water solution, and the ultrasonic frequency at which the waveguide assembly 16 is to be operated (i.e., the predetermined frequency) is about 20 kHZ, one or more of the agitating members 50, 50' are suitably constructed to provide a vibrational displacement of at least 1.75 mils (i.e., 0.00175 inches, or 0.044 mm) to establish a cavitation mode of the agitating members. It is understood that the waveguide assembly 16 may be configured differently (e.g., in material, size, etc.) to achieve a desired cavitation mode associated with the particular gas-liquid solution being treated. For example, as the viscosity of the gas-liquid solution being treated changes, the cavitation mode of the agitating members may need to be changed.

Ultrasonic cavitation refers to the formation, growth and implosive collapse of bubbles in the solution due to ultrasonic energization thereof. Such cavitation results from pre-existing weak points in the solution, such as gas-filled crevices in suspended particulate matter or transient microbubbles from prior cavitation events. As ultrasound passes through the solution, the expansion cycles exert negative pressure on the solution, pulling the molecules away from one another. Where the ultrasonic energy is sufficiently intense, the expansion cycle creates cavities in the solution when the negative pressure exceeds the local tensile strength of the solution, which varies according to the type and purity of solution.

Small gas bubbles formed by the initial cavities grow upon further absorption of the ultrasonic energy. Under the proper conditions, these bubbles undergo a violent collapse, generating very high pressures and temperatures. In some fields, such as what is known as sonochemistry, chemical reactions take advantage of these high pressures and temperatures brought on by cavitation. In addition, the growth and violent collapse of the bubbles themselves provides a desirably rigorous agitation of the gas-liquid solution.

In particularly suitable embodiments, the cavitation mode of the agitating members 50, 50' corresponds to a resonant mode of the agitating members whereby vibrational displacement of the agitating members is amplified relative to the displacement of the ultrasonic horn 32. However, it is understood that cavitation may occur without the agitating members 50, 50' operating in their resonant mode, or even at a vibrational displacement that is greater than the displacement of the ultrasonic horn 32, without departing from the scope of this disclosure.

In general, the ultrasonic horn 32 may be constructed of a metal having suitable acoustical and mechanical properties. Examples of suitable metals for construction of the ultrasonic horn 32 include, without limitation, aluminum, monel, titanium, stainless steel, and some alloy steels. It is also contemplated that all or part of the ultrasonic horn 32 may be coated with another metal such as silver, platinum, gold, palladium, lead dioxide, and copper to mention a few. In one particularly suitable embodiment, the agitating members 50, 50' are constructed of the same material as the ultrasonic horn 32, and are more suitably formed integrally with the ultrasonic horn. In other embodiments, one or more of the agitating members 50, 50' may instead be formed separate from the ultrasonic horn 32 and connected thereto.

While the agitating members 50, 50' (e.g., the rings) illustrated in FIG. 1 are relatively flat, i.e., relatively rectangular in cross-section, it is understood that the rings may have a cross-section that is other than rectangular without departing from the scope of this disclosure. The term "cross-section" is used in this instance to refer to a cross-section taken along one transverse direction (e.g., radially in the illustrated embodiment) relative to the ultrasonic horn's outer surface 34. Additionally, although the agitating members 50 (e.g., the rings) illustrated in FIG. 1 are constructed only to have a transverse component, it is contemplated that one or more of the agitating members 50' may have at least one longitudinal (e.g., axial) component to take advantage of transverse vibrational displacement of the ultrasonic horn 32 (e.g., at and near the nodal region of the ultrasonic horn illustrated in FIG. 1) during ultrasonic vibration of the waveguide assembly 16 (e.g., the T-shaped agitating member).

A baffle assembly, generally indicated at 60, is suitably disposed within the interior space 14 of the housing 12, and in particular generally transversely adjacent the inner surface 36 of the sidewall 30 of the housing and in generally transversely opposed relationship with the ultrasonic horn 32. In one suitable embodiment, the baffle assembly 60 comprises one or more baffle members 62 extending at least in part transversely inward from the inner surface 36 of the sidewall 30 of the housing 12 toward the ultrasonic horn 32. More suitably, the one or more baffle members 62 extend transversely inward from the housing's inner surface 36 to a position longitudinally intersticed with the agitating members 50, 50' that extend outward from the outer surface 34 of the ultrasonic horn 32. The term "longitudinally intersticed" is used herein to mean that a longitudinal line drawn parallel to the longitudinal axis of the ultrasonic horn 32 passes through both the agitating members 50, 50' and the baffle members 62. As one example, in the illustrated embodiment the baffle assembly 60 comprises four, generally annular baffle members 62 (i.e., extending continuously about the ultrasonic horn 32) longitudinally intersticed with the five agitating members 50, 50'.

It will be appreciated that the baffle members 62 thus extend into the flow path 38 of gas-liquid solution flowing within the interior space 14 of the housing 12 past the ultrasonic horn 32 (e.g., within an ultrasonic treatment zone). As such, the baffle members 62 inhibit the gas-liquid solution against flowing along the inner surface 36 of the housing's sidewall 30 past the ultrasonic horn 32, and more suitably the baffle members facilitate the flow of the gas-liquid solution transversely inward toward the ultrasonic horn for flowing over the agitating members 50, 50' of the ultrasonic horn to thereby facilitate ultrasonic energization (i.e., agitation) of the gas-liquid solution.

It is contemplated that the baffle members 62 need not be annular or otherwise extend continuously about the ultrasonic horn. For example, the baffle members 62 may extend discontinuously about the ultrasonic horn 32, such as in the form of spokes, bumps, segments or other discrete structural formations that extend transversely inward from adjacent the inner surface 36 of the sidewall 30 of the housing 12. The term "continuously" in reference to the baffle members 62 extending continuously about the ultrasonic horn 32 does not exclude a baffle members as being two or more arcuate segments arranged in end-to-end abutting relationship, i.e., as long as no significant gap is formed between such segments. Suitable baffle member configurations are disclosed in U.S. application Ser. No. 11/530,311 (filed Sep. 8, 2006), which is hereby incorporated by reference to the extent it is consistent herewith.

While the baffle members 62 illustrated in FIGS. 1-3 are each generally flat, e.g., having a generally thin rectangular cross-section, it is contemplated that one or more of the baffle members may each be other than generally flat or rectangular in cross-section to further facilitate the flow of gas bubbles within the interior space 14 of the housing 12. The term "cross-section" is used in this instance to refer to a cross-section taken along one transverse direction (e.g., radially in the illustrated embodiment, relative to the ultrasonic horn's outer surface 34).

As illustrated in FIG. 1, the gas treatment system 10 further comprises a gas delivery system that is operable to direct the gas into the interior space 14 of the housing 12 from a continuous gas source 86, e.g., ambient air. In one suitable embodiment, the gas delivery system comprises one or more gas pumps 88 (one gas pump being illustrated in FIG. 1) operable to pump the gas from the continuous source 86 thereof to the inlet end 18 of the housing 12 via suitable conduits (not shown). It is understood that the gas delivery system may be configured to deliver gas from more than one source 86 to the housing without departing from the scope of this disclosure. In one specific application, as noted above, ambient air is treated to kill, remove, and/or oxidize organics and/or microorganisms present in the air. In this application, gas pump 88 can be used to deliver ambient air to the interior space 14 of the housing 12 at a generally continuous flow. It is understood, however, that gas can be delivered to the housing 12 from a finite source, such as a gas cylinder or other container, without departing from the scope of this invention. That is, the gas treatment system 10 can be operated to treat batches of gases.

The illustrated gas treatment system also comprises a liquid delivery system. In one suitable embodiment, the liquid delivery system is a generally closed, continuous flow system in which liquid is cycled through the interior space 14 of the housing 12. The liquid delivery system suitably comprises a liquid pump 89, a particulate filter 91, a heat exchanger 93, and suitable conduit (not shown). The liquid pump 89 draws liquid from the interior space 14 of the housing 12 through the liquid outlet port 25 and drives the liquid through the particulate filter 91, the heat exchanger 93 and back into the interior space 14 of the housing 12. A suitable liquid supply 95 provides a sufficient amount of the liquid to the gas treatment system 10. It is understood that the liquid delivery system can have more of fewer components without departing from the scope of this invention.

It is also contemplated that the liquid delivery system can be an open loop system wherein a continuous supply of liquid is delivered to the interior space 14 of the housing 12 via the liquid inlet port 23, and the liquid exiting the interior space of the housing via the liquid outlet port 25 is discharged to a suitable container, treatment system, or drain. It is also contemplated that in some embodiments of the gas treatment system 10 the liquid delivery system can be omitted. In this configuration, the liquid is contained within the interior space 14 of the housing 12.

The particulate filter 91 is provided to remove particulate matter (e.g., suspended solids) from the liquid. The particulate filter 91 can include one or more filter units, for example, in the one embodiment, a first filter unit may be constructed to filter out particles sized greater than about 0.5 microns and a second filter unit downstream from the first filter unit may be constructed to further filter out particles sized greater than about 0.2 microns. It is understood, however, that only one, or more than two filter units may be used, or that the filter units may be omitted altogether. The heat exchanger 93 is provided to alter and/or maintain the temperature of the liquid (e.g., cool the liquid), which may be elevated after passing through the interior space 14 of the housing 14.

In one suitable embodiment, the gas treatment system further comprises an ultraviolet light source 66 for emitting ultraviolet light to irradiate the gas-liquid solution received in the interior space 14 of the housing 12 as it flows through the interior space. In one suitable embodiment, the ultraviolet light source 66 is positioned for emitting ultraviolet light substantially throughout the entire interior space 14 of the housing 12. For example, the ultraviolet light source 66 may have a length that is substantially equal to the length of the housing 12 and is positioned for emitting ultraviolet light into the interior space 14 along the length of the housing. In another configuration and as illustrated in FIG. 1, one or more reflectors (not shown) may be disposed relative to the interior space 14 of the housing 12 to deflect ultraviolet light emitted by the ultraviolet light source 66 throughout the length of the interior space of the housing. In this configuration, the length of the ultraviolet light source 66 can be substantially less than the length of the housing 12.

As seen in FIG. 1, the ultraviolet light source 66 is suitably disposed exterior of the housing 12 and is positioned adjacent the transparent portion 26 thereof (i.e., the portion of the housing constructed of quartz glass). The transparent portion 26 of the housing 12 is thus sized and shaped for allowing substantially all of the ultraviolet light emitted by the ultraviolet light source 66 into the interior space 14 of the housing 12. It is understood that the transparent portion 26 may comprise only a portion of the housing 12 or that it may comprise the entire housing and remain within the scope of this disclosure.

As illustrated in FIG. 1, the ultraviolet light source 66 is positioned to emit ultraviolet light into the interior space 14 of the housing 12 toward the outlet end 20 thereof and just beyond the terminal end 28 of the ultrasonic horn 32. Gas-liquid solution passing through the interior space 14 of the housing 12 adjacent the ultraviolet light source 66 is first highly energized (e.g., at least agitated and more suitably subjected to cavitation) by the ultrasonic horn 32. While the ultraviolet light is deflected or otherwise irradiated throughout the interior space 14 of the housing 12, the most intense region of ultraviolet light is generally adjacent the outlet end 20 of the housing. It is contemplated that a baffling system (not shown) can be disposed within the interior space 14 of the housing 12 adjacent the outlet end 20 thereof to provide a tortuous flow path for the gas-liquid solution thereby increasing the dwell time during which the air-liquid solution is subjected to ultraviolet light.

In one suitable embodiment, the ultraviolet light source 66 is operable to emit ultraviolet light at a wavelength in the range of about 172 nanometers and about 600 nanometers. More suitably, e.g., the light source 66 is operable to emit light at a wavelength in the range of about 172 nanometers to about 300 nanometers where the gas-liquid solutions to be treated is relatively colorless or near colorless. In another suitable embodiment, the ultraviolet light source 66 is operable to emit ultraviolet light at a wavelength in the range of about 300 nanometers to about 600 nanometers for gas-liquid solutions having color and highly viscous gas-liquid solu- tions. The ultraviolet light source 66 is operatively connected to a suitable power supply unit 70 for supplying sufficient electrical power to the ultraviolet light source to generate and emit ultraviolet light into the interior space 14 of the housing 12. It is contemplated that the ultraviolet light source 66 can be omitted from some configurations of the gas treatment system 10 and remain within the scope of the present invention.

The gas treatment system 10 in one particularly suitable embodiment comprises an oxidizing agent source for delivering an oxidizing agent into the interior space 14 of the housing 12. For example, hydrogen peroxide and ozone may each be delivered into the interior space 14 of the housing 12. The hydrogen peroxide is delivered using a suitable pump 72, which delivers hydrogen peroxide from a supply container 74 and directs the hydrogen peroxide through a hydrogen peroxide inlet port 76 into the interior space 14 of the housing 12. Hydrogen peroxide ($H_2O_2$) decomposes to hydroxyl radicals (.OH), as shown below. The hydroxyl radical is an aggressive oxidant that reacts with organics.

$$H_2O_2 \rightarrow 2(.OH)$$

An ozone generator 80 is provided in the gas treatment system 10 to generate ozone for delivery into the interior space 14 of the housing 12 through an ozone inlet port 82. Ozone ($O_3$) decomposes in water to form a superoxide radical ion ($O_2^-$), which is a strong oxidizing agent, and a hydroperoxide radical ($O_2H$). The hydroperoxide radical further decomposes to form another superoxide radical ion ($O_2^-$) and a hydrogen ion ($H^+$).

$$O_3 + OH^- \rightarrow O_2^- + O_2H$$

$$O_2H \leftrightarrow O_2^- + H^+$$

It is contemplated that either one of the hydrogen peroxide and the ozone may be used by itself in the gas treatment system 10 within the scope of this disclosure. It is also contemplated that other oxidation agents may be used or that, in some embodiments, the oxidation agents may be omitted altogether.

The hydrogen peroxide and ozone are delivered in the illustrated embodiment into the liquid intake zone 29 adjacent the inlet end 18 of the housing 12 where they are mixed with the gas and liquid entering the interior space via the inlets 22, 23 to form the gas-liquid solution. The gas-liquid solution flows along the flow path 38 (upward in the orientation of the illustrated embodiment) past the ultrasonic horn 32 where it is ultrasonically energized by the ultrasonic horn, agitating members 50, 50', and baffle members 62 to thereby agitate and more suitably cavitate the solution. The solution in its cavitated state is irradiated by ultraviolet light emitted by the ultraviolet light source 66.

In operation according to one embodiment of the gas treatment system 10 of the present disclosure, the gas treatment system is used to treat organics and/or microorganisms in a gas, and more suitably, ambient air. Specifically, ambient air is delivered (e.g., by the gas pump 88 described above) via conduits to one or more gas inlet ports 22 formed in the housing 12. Water, or other liquid, is also delivered (e.g., by the liquid pump 89 described above) via conduits to one or more liquid inlet ports 23 formed in the housing 12. Ozone and hydrogen peroxide are delivered into the housing 12 to mix with the ambient air and water. As the ambient air enters the interior space 14 of the housing 12 via the gas inlet port 22, the orientation of the inlet port can induce a relatively swirling action thereby mixing the ambient air, ozone, hydrogen peroxide, and water together to form an air-water (i.e., gas-liquid) solution. It is contemplated that one or more of the components used to form the air-water solution can be mixed together before being delivered to the interior space 14 of the housing 12.

The air-water solution flows upward within the interior space 14 of the housing 12 and past the waveguide assembly 16, and more particularly the ultrasonic horn 32. The ultrasonic horn 32 is driven by the drive system to vibrate at a predetermined ultrasonic frequency. In response to ultrasonic excitation of the ultrasonic horn 32, the agitating members 50, 50' that extend outward from the outer surface 34 of the ultrasonic horn dynamically flex/bend relative to the ultrasonic horn, or displace transversely (depending on the longitudinal position of the agitating member relative to the nodal region of the ultrasonic horn).

The air-water solution flows longitudinally upward along the flow path 38 between the outer surface 34 of the ultrasonic horn 32 and the inner surface 36 of the housing's sidewall 30 so that the ultrasonic vibration and the dynamic motion of the agitating members 50, 50' agitate the air-water solution and more suitably cause cavitation in the air-water solution. The baffle members 62 of the baffle assembly 60 disrupt the longitudinal flow of the air-water solution along the inner surface 36 of the housing's sidewall 30 and repeatedly direct the flow transversely inward to flow over the vibrating agitating members. As mentioned above, the ultrasonic horn 32 causes the cavitation in the air-water solution which enhances the treatment of the air by the hydrogen peroxide and the ozone. The air-water solution, while it is cavitated (i.e., energized), flows past the ultraviolet light source 66. The ultraviolet light source 66 irradiates the gas-liquid solution for further treatment.

The use of ultraviolet light in this system 10 increases the efficiency and the efficacy of the degradation of the impurities in the air-water solution. First, the ultraviolet light photochemically cleaves some of the ozone and peroxide agents to produce higher concentrations of the superoxide and radicals which work in conjunction with the sonochemistry to break down the impurities in the air-water solution. Secondly, the nature of the high energy ultraviolet light starts the breakdown of the impurities by their absorption of the radiation followed by scission of the chemical bonds. For example, with respect to dyes and other colored agents, the sonochemistry will further breakdown these compound fragments, due to these intermediates being chemically unstable and therefore it is easier for them to undergo further degradation in the ultrasonic system.

An ultraviolet lamp of the ultraviolet light source 66 can be adjusted to produce either a broad ultraviolet light emission or specific narrower wavelength range by careful selection of the lamp bulb. For example, Fusion UV Systems, Inc. of Gaithersburg, Md. offers a series of ultraviolet lamp bulbs with the following emission ranges:

H-bulb 210-315 nanometers
D-bulb 350-450 nanometers
V-bulb 400-450 nanometers
M-bulb 365 nanometers and 406 nanometers.

After treatment, the gas and liquid phases of the air-water solution are separated. The air exits the interior space 14 of the housing 12 through the gas outlet port 24. The air, which has been rid of impurities, is conditioned for any suitable use, e.g., respiratory air for a medical patient. The separated water exits the interior space 14 of the housing 12 through the liquid outlet port 25. More specifically, the water is drawn from the housing 12 by the liquid pump 89. The water is then driven through the particulate filter 91, the heat exchanger 93, and back into the interior space 14 of the housing 12 where it is again mixed within incoming ambient air.

The gas treatment system 10 may also optionally be combined with a gas post-processing system in fluid communication with the outlet end 20 of the housing for further processing the ambient air after the air exits the housing. For example, one or more air filter units 100 may be disposed along the air flow path downstream of the housing 12 to filter out particulate material, such as dirt, debris or other contaminates that may be present in the air. It is understood that the filter units may be omitted altogether.

In one embodiment, such as when hydrogen peroxide is introduced into the housing 12 to be used as an oxidizing agent for removing impurities from the gas, the residual hydrogen peroxide may need to be removed from the exit stream by a post processing unit that reacts with the hydrogen peroxide. For example, this post processing unit may include a platinum or silver surface (not shown) that decomposes any residual hydrogen peroxide. Similarly, when ozone is introduced to aid in the removal of impurities, a post processing unit, such as a destruct unit 102, may be used to decompose any ozone exiting the housing along with the ambient air.

Following treatment and/or post treatment, the cleaned ambient air may be directed to a storage container (e.g., cylinder), used in a process, or directed to an air supply system.

When introducing elements of the present invention or preferred embodiments thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions and methods without departing from the scope of the invention, it is intended that all matter contained in the above description and shown in the accompanying drawings shall be interpreted as illustrative and not in a limiting sense.

What is claimed is:

1. A process for treating a gas, the process comprising:
   delivering a gas to be treated to an interior space of a housing via a gas inlet port of the housing, wherein the gas, as it is delivered to the interior space, includes at least one of microorganisms and organics;
   mixing the gas with a liquid within the interior space of the housing to form a gas-liquid solution;
   ultrasonically energizing the gas-liquid solution within the housing by operating an ultrasonic horn disposed within the interior space of the housing at an ultrasonic frequency to facilitate breaking down of said at least one of microorganisms and organics in the gas of the gas-liquid solution; and
   irradiating the energized gas-liquid solution in the interior space of the housing using an ultraviolet light source to facilitate breaking down of said at least one of microorganisms and organics in the gas of the gas-liquid solution;
   removing the gas from the interior space of the housing via a gas outlet port of the housing after said ultrasonically energizing the gas-liquid solution and said irradiating the energized gas-liquid solution.

2. The process of claim 1 further comprising introducing an oxidizing agent into the interior space of the housing to mix with the gas-liquid solution.

3. The process of claim 1 wherein delivering a gas to be treated to an interior space of a housing comprises delivering air to be treated to the interior space of the housing.

4. The process of claim 3 wherein mixing the gas with a liquid within the interior space of the housing to form a gas-liquid solution comprises mixing air with water within the interior space of the housing to form an air-water solution.

5. The process of claim 1 wherein the ultraviolet light source is located relative to the ultrasonic horn and the gas outlet port such that the ultraviolet light source irradiates the gas-liquid solution while the gas-liquid solution is ultrasonically energized by the ultrasonic waveguide assembly.

6. The process of claim 1 wherein the housing has at least one liquid inlet port for receiving liquid into the interior space of the housing and at least one liquid outlet port for allowing liquid to exit the interior space of the housing, the housing further having an inlet end and an opposite outlet end, wherein the gas inlet port and the liquid inlet port are at the inlet end of the housing, and the gas outlet port and the liquid outlet port are at the outlet end of the housing.

7. The process of claim 6 wherein the housing has a longitudinal axis orientated vertically such that the inlet end of the housing constitutes a lower end and the outlet end of the housing constitutes an upper end.

8. The process of claim 1 wherein the ultraviolet light source is operable to emit ultraviolet light at a wavelength in the range of about 172 nanometers to about 600 nanometers.

9. The process of claim 8 wherein the ultraviolet light source is operable to emit ultraviolet light at a wavelength in the range of about 172 nanometers to about 300 nanometers.

10. The process of claim 8 wherein the ultraviolet light source is capable of emitting ultraviolet light at a wavelength in the range of about 300 nanometers to about 600 nanometers.

11. The process of claim 1 wherein at least a portion of the housing comprises a transparent material for allowing ultraviolet light to irradiate through the housing into the interior space thereof to facilitate said treating of the gas in the gas-liquid solution in the interior space of the housing, the ultraviolet light source being disposed exterior of the housing and adjacent the transparent portion of the housing.

12. The process of claim 1 wherein the ultrasonic horn has an outer surface located for contact with the gas-liquid solution within the housing, and a plurality of discrete agitating members in contact with and extending transversely outward from the outer surface in spaced relationship with each other, the agitating members and the ultrasonic horn being constructed and arranged for dynamic motion of the agitating members relative to the ultrasonic horn upon ultrasonic vibration of the ultrasonic horn.

13. The process of claim 2 wherein the oxidizing agent comprises at least one of hydrogen peroxide and ozone.

14. The process of claim 1 further comprising a gas delivery system for delivering gas to be treated to the interior space of the housing via the gas inlet port, and a liquid delivery system for delivering the liquid to the interior space of the housing via the liquid inlet port.

15. The process of claim 1 wherein the housing comprises a mixing zone for mixing the gas and the liquid.

16. The process of claim 1 further comprising a liquid delivery system for delivering liquid into the interior space of the housing.

17. The process of claim 16 wherein the housing has at least one liquid inlet port for receiving liquid into the interior space of the housing and at least one liquid outlet port for allowing liquid to exit the interior space of the housing, wherein the liquid delivery system is a closed loop system in which liquid is caused to flow through the housing generally from the liquid inlet port to the liquid outlet port and flow exterior of the housing generally from the liquid outlet port back to the liquid inlet port.

18. The process of claim 17 wherein the liquid delivery system comprises a pump and a heat exchanger.

19. The process of claim 14 wherein the gas delivery system comprises a gas pump.

20. The process of claim 14 wherein the liquid delivery system is a closed loop system in which the liquid is caused to flow through the housing generally from the liquid inlet port to the liquid outlet port and flow exterior of the housing generally from the liquid outlet port back to the liquid inlet port.

21. The process of claim 20 wherein the liquid delivery system comprises a pump and a heat exchanger.

22. The process of claim 21 wherein the liquid delivery system further comprises a particulate filter.

\* \* \* \* \*

UNITED STATES PATENT AND TRADEMARK OFFICE
CERTIFICATE OF CORRECTION

| | |
|---|---|
| PATENT NO. | : 8,454,889 B2 |
| APPLICATION NO. | : 11/963237 |
| DATED | : June 4, 2013 |
| INVENTOR(S) | : Robert Allen Janssen et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 610 days.

Signed and Sealed this
Sixth Day of January, 2015

Michelle K. Lee
*Deputy Director of the United States Patent and Trademark Office*